United States Patent [19]

Hampicke

[11] 4,140,116

[45] Feb. 20, 1979

[54] LEG OR FOOT BANDAGE, ESPECIALLY FOR HORSES

[76] Inventor: Willi Hampicke, Kreuzbroicher Str. 45, Leverkusen, Fed. Rep. of Germany, 5090

[21] Appl. No.: 783,206

[22] Filed: Mar. 31, 1977

[30] Foreign Application Priority Data

Mar. 31, 1976 [DE] Fed. Rep. of Germany ....... 2613777

[51] Int. Cl.[2] .......... A61F 13/00

[52] U.S. Cl. .......... 128/165; 54/82

[58] Field of Search .......... 128/87, 89, 82, 83, 128/80 R, 165; 54/82

[56] References Cited

U.S. PATENT DOCUMENTS

| | | | |
|---|---|---|---|
| 1,479,000 | 1/1924 | Keller | 54/82 |
| 2,937,487 | 5/1960 | Dever | 54/82 |
| 3,020,658 | 2/1962 | Clark | 40/21 C |
| 3,279,107 | 10/1966 | Baumgartner | 40/21 C |
| 3,405,506 | 10/1968 | Kostur | 54/82 |
| 3,717,145 | 2/1973 | Berndt et al. | 128/402 X |

*Primary Examiner*—John D. Yasko
*Attorney, Agent, or Firm*—Michael J. Striker

[57] ABSTRACT

A bandage, especially for application around a horse's foot or leg to afford protection and support and/or means for treatment with medication, and comprising: first, a tough flexible dense plastic outside layer backing sheet with a plurality of closure elements projecting from one sheet margin, for closure engagement with cooperative means spaced inward from the opposite margin, and secondly, a preferably perforated inner layer of foamed-plastic either in a continuous layer or in discrete strips, whereby there is afforded some contour accommodation to the leg or foot member on which used.

18 Claims, 20 Drawing Figures

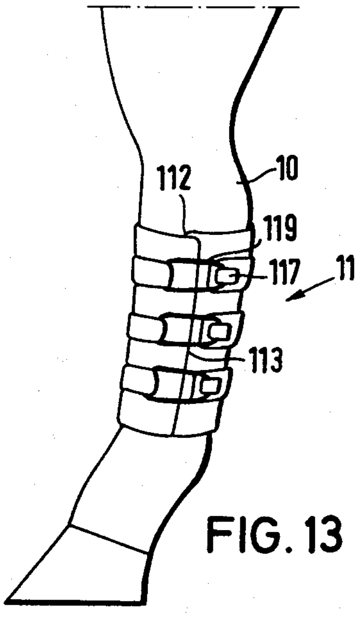
FIG. 13
FIG. 14
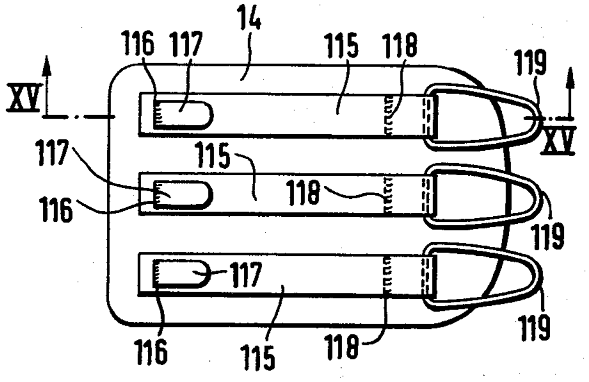
FIG. 15
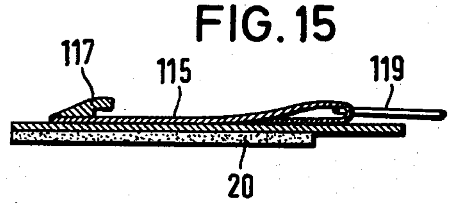
FIG. 17
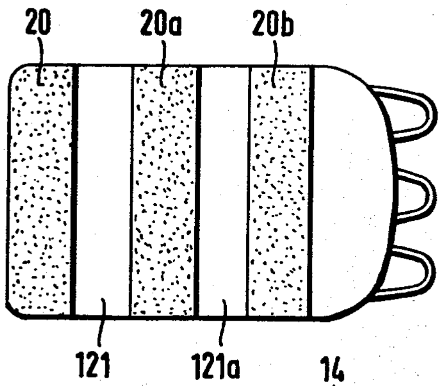
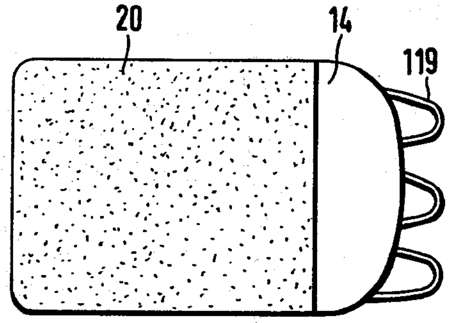
FIG. 16
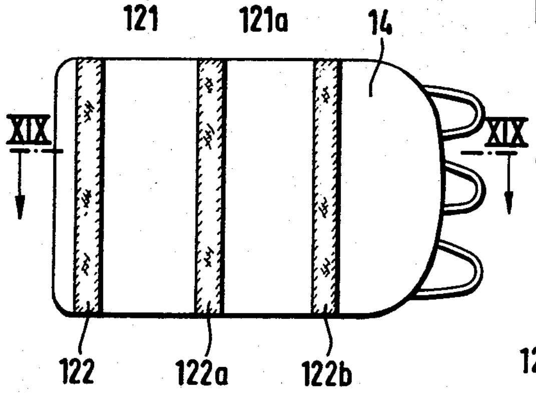
FIG. 18
FIG. 19
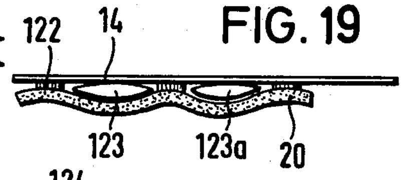
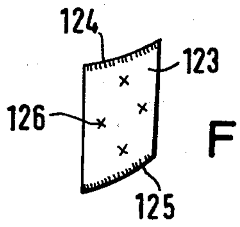
FIG. 20

LEG OR FOOT BANDAGE, ESPECIALLY FOR HORSES

The present invention is concerned with a bandage applicable especially to a horse's foot or leg to offer a supportive or protective function, and which alternatively or conjunctively may serve for treatment with medicaments.

Especially in the case of jumpers and horses trained in similar competitive activities, there are always present the dangers of torn ligaments, sprains, and other injuries, which make it necessary by bandages to support and to treat the most endangered parts of the animal's legs.

Bandages hitherto known for this purpose are more or less elastic bands applied in numerous turns wrapped about the foot or about the most endangered parts of the leg. However, a secure emplacement and seating of the bandage has been a constant problem, arising in part from difficulties in fastening of the ends, so that on the one hand a bandage in no case be loose, yet on the other be not so tight as to be uncomfortable for the animal.

These same considerations apply for cases of injuries, as well as application of bandages for support or protective purposes or of bandages which carry a healing salve or other medicaments.

The general object of the present invention is to provide a foot or leg bandage for horses, which can be applied more or less firmly and tightly as may be required; and which nonetheless permits to the animal a certain degree of freedom of movement. Another object is to provide a bandage which moreover better fits the external shape of the leg or foot, and permits medicinal treatment of the leg.

A still further object is to provide a bandage of the type described which is simple in fabrication and use.

For the attainment of one or more of these objects, by the present invention, there is proposed a bandage structure constituted of an outer layer or backing sheet of solid plastic and an inner layer or lining of a softer plastic, such as a foam plastic, for which an open-celled type foam is often preferred.

The use of the firmer, more solid plastic, in the outer layer, and of the softer plastic for the inner layer affords a more secure seating of the bandage along with a good fit or adaptation to the leg shape. At the same time, the plastic construction affords a bandage which is both easy to clean, and also has a long useful life.

The plastic of the outer layer or member may be comparatively stiff or rigid, to the extent that, as fabricated, it has a shape which is adapted to the external shape of the animal's foot or leg. Thus, for example, the outer member may be produced by injection molding, e.g., from a soft elastic plastic, if a sufficient flexibility is conferred, so that the support (which is not comprised of a closed ring-shaped structure) is so far spreadable that it can be drawn over the leg.

Also a bandage of this type is provided with closure elements, in order to obtain a firm seating or application to the leg or foot of the animal.

Especially advantageously, the outer layer is comprised of thick, thermoplastic synthetic plastic sheet, which is specified as comparatively soft; whereby there is conferred a high adaptability of the backing sheet to the shape of a leg to be treated in combination with a certain extensibility of the sheet.

By a further proposal of the invention, to attain an especially advantageous and simple fastening of the bandage, on the outer surface of the outer layer, by adhesives or thermo plastic welding there are bonded strips of heavier plastic sheet stock, which, when the bandage is applied, run circumferentially as securing straps and these strips carry appropriate fastening or closure elements.

As one type of closure, plastic elements of hook-like form may be applied in strip end regions where the strips are welded onto the outer layer; while at the other free ends of the strips, there are disposed respective elastic rings which are engageable in the aforementioned hooks. This arrangement attains a secure yet yieldable fastening, which especially assures holding securely even under the stresses of riding, particularly in difficult terrain with the diverse weathering conditions there usually present. The fastening as such is water-proof, durable and easy to handle.

By another modification, on the inner side of the outer layer, especially advantageously at localized positions, there be disposed one side of interpenetrating bristle-type fastening or closure means (of the type represented, for example, by closures sold in the United States of America under the mark "VELCRO"). These have the advantage that on the inner side of the outer layer, there may be secured, in an easily releasable and changeable manner, inserts of different thickness, and bearing of course cooperating closure portions. Thus also the inner layer of foam or soft plastic may be similarly secured to the backing, by such means. In place of the foam layer, however, at localized places, there can be also used respective cushions, especially such as may serve for treatment by medicinal means.

Also at one of the vertical or overlapping margins of the outer sheet, a plurality of tongue-like projections on their inner surfaces are provided with respective bristle-closure elements. On the opposed margin there is welded or otherwise bonded a plastic strip, which forms a flap directed toward the margin of the outer layer; and the region of the outer-sheet overlapped by this flap, and also the opposed inner face of this flap itself, are likewise covered with said bristle-closure material, so that cooperatively the tongue-like projections, the flap and the flap-covered region serve to provide a secure attachments and firm seating of the bandage on the animal without resort to hook type fasteners. This arrangement is especially suited for therapeutic type bandages.

By a further modification, between the outer or backing layer and an inner soft layer preferably constituted of foamed-plastic, there is present a flexible container for medicinal material, which container especially advantageously is comprised of a thermoplastic synthetic plastic film bag to contain medicinal means — liquids, pastes or salves, or powdered material — effective for the treatment of the leg. So that the medicament can reach the leg, the bags have perforations made therein shortly before each bag is inserted between the backing layer and the animal's leg.

Furthermore to hinder soaking of the bandage inner layer through the animal's sweating, the innermost layer is constituted of a soft plastic sheet having spaced parallel passages or grooves in its inner and outer faces, which passages extend parallel to the leg, and preferably are arranged in opposed inner and outer passage pairs, between which open perforations through the inner layer.

Thus sweat is led both directly along the animal's leg, and also, after passage through the perforations, along external passages, to the margin of the bandage in a downward direction in liquid form; and also water vapor may escape upwardly and outwardly by those passages. There is the advantage also that the bandage can be easily kept clean by water washing and is easily dried because of the passage arrangement.

This latter particular structure is readily attained by providing the inner layer as a soft synthetic plastic mat having, running longitudinally in what will be a direction parallel to the leg, passage-forming grooves opposed on opposite sides of the mat, with more or less regularly distributed perforations opening through these groovings. Though they may be round, especially advantageously the perforations are rectangular and in section extend over the entire width of the groovings, for maximum flow. The passages and perforations are especially advantageously obtained in the mat form by a stamping operation.

Further advantageously, transverse to the passages and in the region between the perforations, internal reinforcing fibers are present, to confer a particularly high strength on the mat.

A particularly useful embodiment of the bandage invention involves the following structure: (a) an outer layer of transparent solid plastic; (b) on the inner side of the latter a woven-layer; (c) a plurality of bands on the woven layer, of which each band at one end is by rivets connected with a closure element disposed on the outer surface of the outer layer, and of which the other end is led outwardly through a slit in the woven-layer and of the outer layer; (d) at localized places on the woven-layer, plastic foam bodies are applied; and (e) a soft, permeable inside layer is present.

Between the transparent outer layer and the woven-layer lying therebehind, there may further be disposed a symbol-bearing layer. It is understood that this structure is particularly advantageous, for it is possible with a non-transparent solid plastic layer to eliminate the woven-layer otherwise used there-behind. But still especially advantageous is the transparent outer layer, because, permits by simple means the placement of colored symbols behind this outer layer and before the woven-layer, for example, the colors of the club or of the horse-owner; or colored stripes or other such symbols, which designate the owner or perhaps his nationality.

By another aspect of the invention, it is proposed that in the region of the upper rim of the inner layer, by an outward folding over, there be a doubling in thickness to provide a cushioning, which does not detract from the effectiveness for drainage or evaporation of liquid such as sweat. To improve the cushioning effect, it is further proposed that the overfold of the inner layer project slightly above the shape or contour of the outer layer.

By modification of another aspect of the invention, the fasteners take the form of lever clasps, which permit stepless adjustment in the tension of a respective closure band corresponding to actual requirements.

By a further particular proposal, each clasps is comprised of a U-shaped base element, of which the base plate is secured on the bandage by a rivet pair and of which the two legs are provided with aligned perforations in which the pivots of a clamping lever are engaged. The lever comprises a grip part to be hand-grasped and at an angle thereto a clamping leg. For particular strength of the closure, in a particular form the pivots are integral with the clamping lever; and each side of the grip part is provided with a right-angle bent integral cheek piece, which pieces at the closed position of the element embrace the legs of the U-shaped base element.

Other objects and advantages will appear from the following description and the drawings wherein FIG. 1 is a fragmentary side view of a horse's leg with an applied bandage;

FIG. 13 shows a still different bandage form as applied to an animal's leg;

FIG. 14 shows the bandage of FIG. 13 flattened, and as viewed from the outside;

FIG. 15 is a horizontal sectional view taken at XV—XV in FIG. 14;

FIG. 16 is an inside view corresponding to FIG. 14;

FIG. 17 is a view similar to FIG. 16, showing a modification;

FIG. 18 is a view similar to FIG. 16, showing a further modification with a portion omitted;

FIG. 19 is a fragmentary horizontal sectional view taken at about the line XIX—XIX in FIG. 18;

FIG. 20 is an enlarged detail of a bag pertaining to FIGS. 18–19.

BANDAGE OF FIGS. 1–8

Figure 1:
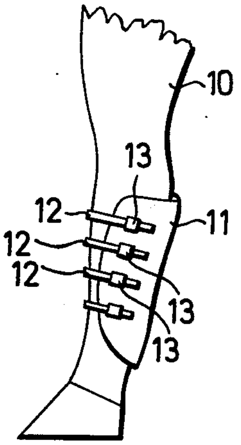
Figure 2:
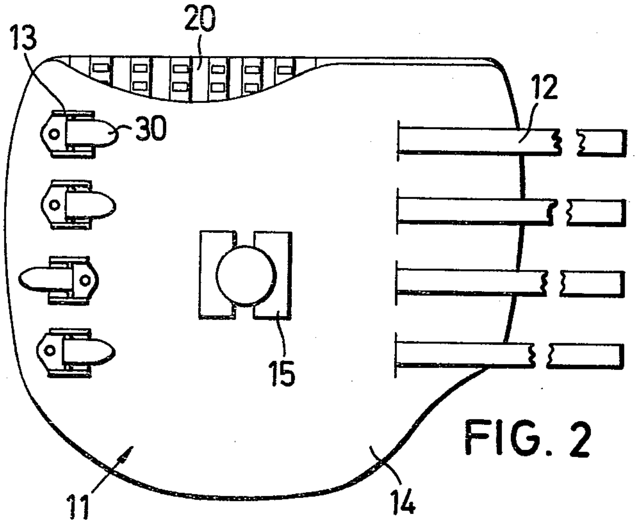
FIG. 2 is a plan view of a bandage laid out flat with the outside exposed.

The preferred form of bandage 11, appearing in FIG. 1 as applied to the leg 10 of an animal such as a horse, and there secured by straps 12, held by respective buckles or lever clasps 13, is shown in greater detail in FIG. 2 et seq. Though the bandage of FIG. 1 encircles only a part of the leg circumference, it may be made broader as required to embrace a larger portion of the leg or even to overlap at vertical margins; and, of course may be made longer with more clasps to overwrap a greater length of the leg.

Figure 6:
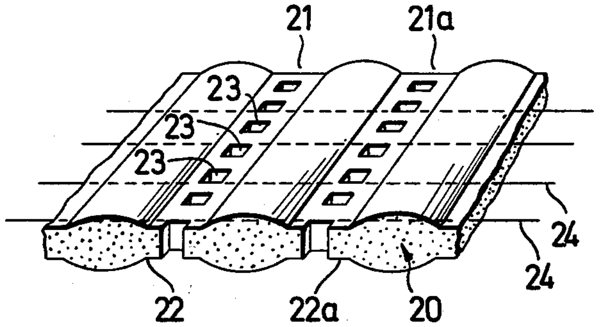
FIG. 6 is an enlarged fragmentary perspective view of one form of inner layer or sheet.

The bandage structure then basically comprises an outer preferably transparent layer or backing sheet 14 of thermoplastic material of which the adhesiveness developed by mild warm-air heating is sufficient to bond thereto the symbol layer material 15, the latter being applied to the inner face of 14; then as a next inward layer, a covering layer 16 comprised of a plastic-coated woven material layer; the straps 12 with buckles 13; and finally as the innermost layer or sheet a mat structure 20 of soft plastic, for which particulars of preferred structure are given relative to FIG. 6.

Figure 4:
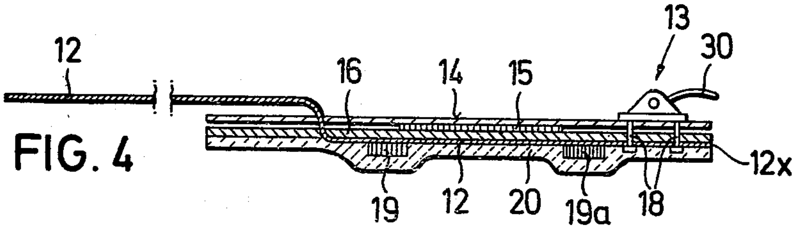
FIG. 4 is a horizontal section taken as indicated by the line IV—IV in FIG. 3.
Figure 5:
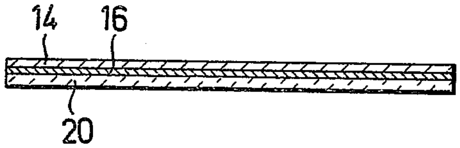
FIG. 5 is a horizontal section taken as indicated by the line V—V in FIG. 3.

The symbol material 15 may be quite localized as is shown in FIGS. 2 or 4, or wider in area even to the extent of constituting a substantially complete layer of thermoplastic character. At the woven-layer 16, the plastic-coated side faces inwardly; and the layer itself is secured to 14 or to 14–15 through use of a two-component cold-hardening adhesive.

The straps 12 are thermoplastically adhered or welded to the inner side of the woven-layer 16 by application of heat, since the thermoplastically-coated side of 16 is inwardly disposed and the straps themselves are formed of thermoplastic material.

Figure 3:
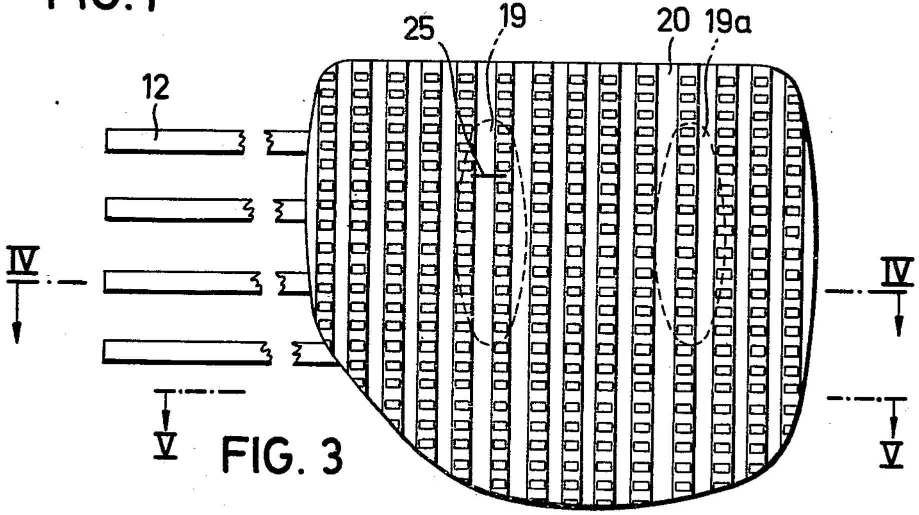
FIG. 3 is an inside view of the bandage of FIG. 2.

It may be here observed that though the symbol material is presented at 15 in FIGS. 2–3 in a localized form, as for example, a coat of arms or like colored symbol, say indicating the nationality or other affiliation of the rider or owner, the symbols may also be constituted of other symbol material, for example, stripes extending over the entire width of the bandage.

Inward of the woven-layer 16 and the straps 12 applied thereto, i.e., in effect outward of mat or layer 20, at limited locations, (here two as shown) there are synthetic plastic open-celled foam cushions 19, 19*a*, which extend longitudinally of the bandage and can also serve as medicament reservoirs as later noted.

The inner layer or mat 20, comprised of soft synthetic plastic, which may be an open-celled foam, has on both sides longitudinally running parallel grooving 21, 21*a*, on the upper side and 22, 22*a*, on the other side, that is, the side disposed toward the horse's leg; these groovings or longitudinal recesses extending then in the direction of the leg length when the bandage is in place. Perforations 23 extend from one opposed groove to the other, so that moisture appearing on the horse's leg is conducted away first by the leg-adjacent grooves 22, 22*a*, allowing downward drainage as well as upward and downward water vapor escape, and of course, further moisture escape through the perforations 23 to groovings 21, 21*a* for similar drainage or dissipation there. The straps 12, however, despite location do not block this action. Reinforcement fibers 24, e.g., of nylon, extend transversely of the mat 20, passing through the regions between perforations 23.

The aforementioned cushions or pads 19, 19*a*, may be supplied with medicinal material, through the openings 23 of the mat element or inner layer; but also as indicated in FIG. 3, access to these supply or storage pads may be further afforded by a slit 25 provided through the inner sheet or layer 20 into the upper region of the plastic foam pads or cushions 19. It is observed that the mat-like layer 22 may be produced by what is in effect a punching and pressing operation to produce the perforations 23 as well as the groovings 21, 22, etc.

The outer shape of the bandages is especially readily adapted to conditions of use. To obtain a soft fit in the upper regions, the inner sheet or layer 20 may be doubled in thickness by folding over outwardly, e.g., along a top margin.

The inner layer 20 of the soft, advantageously thermoplastic synthetic plastic, is bonded to the plastic-coated woven material 16 and to the straps 12 through use of heating. Also in cutting the bandage for establishing its outer shape closely to a leg shape, a hot cutting knife is used, so that its heating effect achieves also a joining of cut layers through plastic welding.

Figure 7:
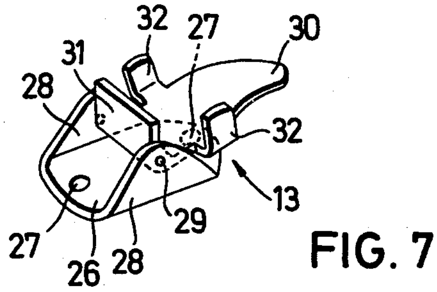
FIG. 7 is a perspective representation of one form of lever closure in released condition.
Figure 8:
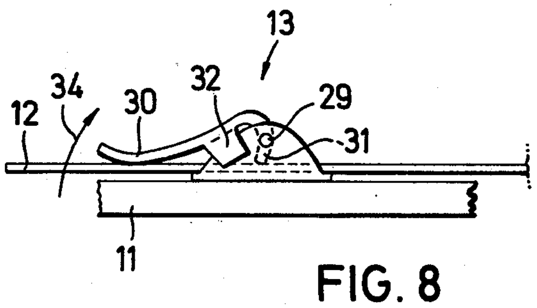
FIG. 8 is a side view showing of the closure of FIG. 7 in relation to certain bandage parts, and in closed condition.
Figure 9:
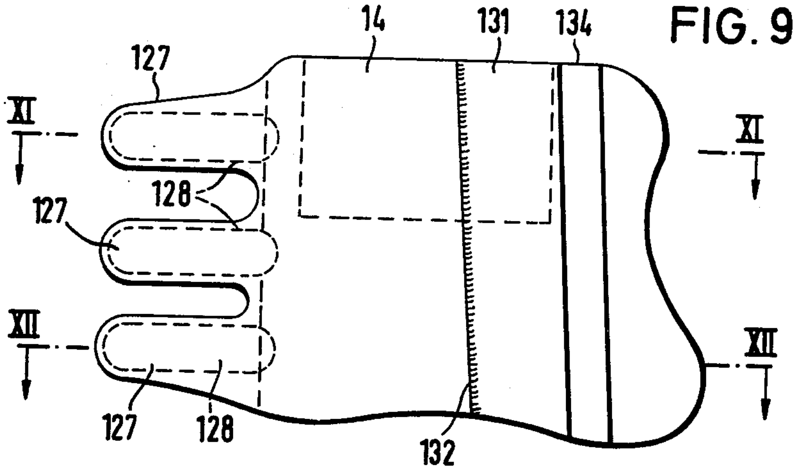
FIG. 9 shows a further bandage form, the bandage being flattened and viewed from the outside.
Figure 10:
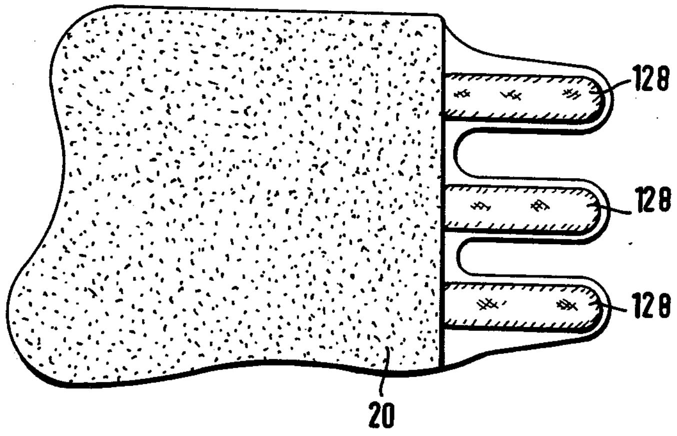
FIG. 10 is an inner side view corresponding to FIG. 9.
Figure 11:
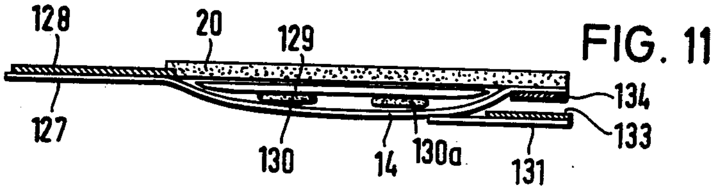
FIG. 11 is a horizontal sectional view taken along the line XI—XI in FIG. 10.
Figure 12:
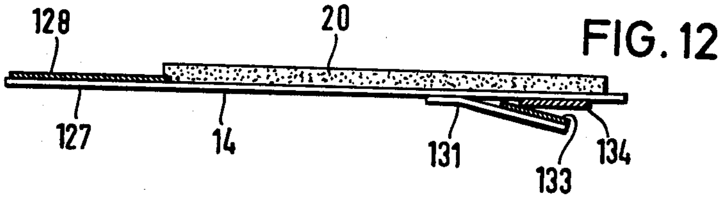
FIG. 12 is a horizontal sectional view taken along the line XII—XII in FIG. 10.

The bandage is secured, of course, through the aforementioned straps 12 engaged in the respective lever clasps or closures 13, one of which is represented in greater detail in FIGS. 7 and 8 (open and clasped respectively). This clasp or buckle form is comprised of a U-shaped base element integrally providing a flat base 26 with two rivet holes 27 and two up-turned side legs 28 with perforations 29, in which are received respective pivots of a lever clasp or clamping element. The latter in turn integrally comprises a hand-grip portion 30 with respective side cheek pieces 32 (which as shown in FIG. 8, at closed position externally embrace the base legs 28) and a strap locking or clamping arm 31 which pinches the strap against the base. As noted in FIG. 8, by the shape of the elements, the loose end of the strap may be lifted in the direction 34, thereby to lift finger lever 30, so that the clasp may be released without attempting to manipulate directly the finger grip portion 30.

BANDAGE OF FIGS. 9–12

In FIGS. 9–12, there appears a bandage form, which does not rely on buckles or clasps and straps, but rather utilizes interengaging-bristle closure means, e.g., of the type widely marketed in the United States under the trademark "VELCRO."

Here again for simplicity of fabrication operations the backing or outer layer 14 is a heavy thermoplastic sheet, 2 to 4mm thick, to which is connected the mat or inner sheet 20 of open-celled synthetic plastic foam. On one margin of the backing piece 14, a margin vertical in use, a plurality of integral tongue extensions 127 are provided on their respective inner sides with bonded-on strips 128 of VELCRO type closure material, while on the outer face of 14 spaced inward along the other margin there is a pair of directly opposed cooperating bristle-closure strips namely, strips 134 bonded to the outside face of backing sheet 14, and, facing 134, a strip 133 carried on a flap strip 131 secured to 14 by a thermoplastic weld 132.

Thus with flap 133 drawn away from 134, as the bandage is wrapped in place, the tongues 127 fall over the closure portion 134 with the cooperating closure portions 128 then retentatively engaging on 134; whereafter the flap 131 is pressed down into place bridging over tongues 127 with the closure strip 131 then cooperatively engaging with strip 134 at the interspace between tongues 127. Thus a very secure closure or attachment is obtained between the connected margins of the bandage.

It should be noted that in the upper region of the bandage, there is a pouch 129 formed of thermoplastic material, which has a bag form for containing and releasing medicament for example similar to that of FIG. 19.

Thus in this pouch a liquid or paste may be introduced of medicinal character. So that the latter last longer, between the pouch 129 and the outer layer 14 there are disposed two strips 130 and 130 of foam or spongy character, which absorb the paste and release it in controlled doses over a longer period of time.

BANDAGE OF FIGS. 13–16

The bandage 11, shown applied to an animal's leg in FIG. 13 with overlapping vertical margins at 112–113 (i.e., margins extending parallel to the leg length), is again comprised basically of the nearly rectangular, 2 to 4mm thick backing sheet 14 and, bonded to 14, a layer 20 of foamed synthetic plastic, which however does not extend over the full face of 14 but as appears in FIGS.

15 and 16 terminates short of the backing end, for adjustment freedom.

The bandage may be made of comparatively soft plastic, and its basic form may be conferred by injection molding of its principal form-determining component, i.e., backing 14, so that from the start in effect it has a shape or contour approximating that of the leg where it is to be used. It is not then closed as a ring or tube, but as indicated is longitudinally open and has the overlapping margins 12–13 held secured to each other in an assured suitable relation, by closure means 115, 116, 117, 118, 119 to be described.

Plastic bands or strips 115, which advantageously may be of the same material as 14, are secured to the outer face of layer 14 by weldings at 116 near one end, this being the sole place of strip bonding, where also respective plastic hooks 117 are weld-secured on the top of the strips. At the other end, each strip is looped back under and welded to itself as at 118; an elongated link "ring" 119 being thus secured within the loop; the link or ring 119 itself being formed of more or less rigid plastic or rubber.

The layer 20 can be bonded to 14 by adhesives, or also by heating of the opposed contacting faces of 14 and 20 so that the sheets are connected by the thermal plastic welding.

The bandage is of course simply applied by wrapping the bandage into place and then stressing bands 115 to allow rings 119 to engage over the hooks 117.

MODIFICATION OF FIGS. 17–20

The bandage of FIG. 17 is basically similar to that of FIGS. 14–16; but the inner or foamed plastic layer 20 is here broken up into three vertical strips 20, 20*a*, 20*b*. Thus when the bandage is emplaced, between these vertical strips there will be formed in effect slots or pouches 121, 121*a* in which may be emplaced medicamental material, for example carried on correspondingly sized cloth strips or the like.

Here again after the bandage is emplaced, a pull is exerted by hand on rings 119 to bring them over the respective hooks 117. With the rings 119 comprised of elastic or other extensible material, and also bands 115 having a certain elasticity and flexibility, a firm and secure yet flexible closure is obtained for the bandage. This flexible action is also to some degree increased through the use of the foam plastic at 20.

MODIFICATION OF FIGS. 18–20.

FIG. 18 shows a general arrangement of backing sheet 14 and closure bands similar to that of FIGS. 14–17. However, on the inner face of backing 14, there are bonded, preferably by adhesives, the spaced vertical bristle-type closure elements 122, 122*a*, 122*b*.

The foam plastic inner sheet 20 appearing in FIG. 19, has similarly spaced cooperating bristle-strips, so that layer 20 may be easily applied to and removed from 14.

In the vertically extending spaces between these vertical regions of connection of 14 and 20, in effect pockets are formed to receive medicament, or sealed pockets 123 of medicamental material as shown in FIG. 20. The latter are simply transversely thermally sealed off at 124 and 125.

For these bags 123, valved bags may be used of known form, which may be furnished filled with liquid or the like, for introduction into the bandage unit, but with no escape through the filling valve. Medicinal materials, in liquid, paste or solid forms, ice-water or the like may be used in bags at these locations.

After the bags are emplaced, they may be pierced as at 126 to release the contained material. Since the layer 20 is comprised of open-celled plastic foam, these materials thus reach the animal's leg. The pores of the foam retain the material well over a long period and uniformly distribute the same over the leg.

What is claimed is:

1. A bandage for application about a leg of an animal, comprising an elongated outer layer; fastening means mounted on said outer layer for securing the bandage in a desired position around the leg of the animal, and an elongated inner layer having respective surfaces facing toward and away from said outer layer, at least one of said surfaces being provided with a plurality of grooves spaced from one another longitudinally of said inner layer and extending substantially transversely to the elongation thereof and substantially lengthwise of the leg when the bandage is applied about the leg, said inner layer being provided with a plurality of throughgoing perforations each having an end communicating with the leg of the animal and another end, to thereby collect the animal's sweat through said perforations and conduct it under the influence of gravity to a respective margin of the inner layer for evacuating from the bandage.

2. A bandage as described in claim 1, wherein
the soft synthetic plastic material, at least in part, is in thick sheet-like form provided with a multiplicity of distributed perforations; and
the said outer layer is comprised of a flexible thick thermoplastic synthetic plastic sheet stock.

3. A bandage as described in claim 2, wherein
said fastening means include, secured in place on the outside or backing layer, a plurality of parallel securing bands, formed of strips of thicker synthetic plastic sheeting,
which strips respectively run circumferentially about the emplaced bandage.

4. A bandage as described in claim 3, wherein
cooperating fastening elements or clasps are disposed at the respective said strips for effectively securing to each other the respective ends of each said band.

5. A bandage as described in claim 1, wherein
the said passages are in laterally parallel spaced relation to each other, and parallel to the length of the leg or foot-enclosing space formed when the bandage is emplaced.

6. A bandage as described in claim 5, wherein
the inner layer is comprised of a soft plastic mat which, running in the direction corresponding to the length of the leg, is provided on opposite sides of the mat with parallel passage-forming opposed grooving,
and said perforations are formed at the location of the opposed grooving.

7. A bandage as described in claim 6, wherein
the said perforations are respectively substantially rectangular in cross-section.

8. A bandage as described in claim 5, wherein
the said passages and perforations are produced by stamping.

9. A bandage as described in claim 6, wherein
the said mat element includes internal reinforcing fibres, running transversely to the direction of the said passages, but located in regions between the said perforations.

10. A bandage, for application about a horse's leg to afford support or protection, and/or to provide medicinal treatment, which bandage as described in claim 5 is comprised of an outer sheet layer of solid synthetic plastic, on which several parallel securing bands are applied with respective fasteners, and an inner layer comprised of a permeable synthetic plastic, wherein:

the outer layer is constituted of a transparent solid synthetic plastic, on the inner side of the outer layer, there is present a woven layer, the said bands are applied on the woven layer, with each band at one end connected through rivet means with the respective cooperative fasteners disposed on the outer surface of the outside or backing layer, and each band at the other end is led outwardly through a slit in the said woven layer and outer layer;

at localized places of the woven layer, foamed plastic bodies are applied, and a soft permeable inner layer is used.

11. A bandage as described in claim 10, wherein between the said outer layer and the woven layer, there is disposed a symbol-bearing layer.

12. A bandage as described in claim 11, wherein in the region of the bandage upper edge, the said inner layer is effectively doubled through an outward overfold of the said inner layer.

13. A bandage as described in claim 12, wherein the overfold of said inner layer projects slightly beyond the contour of the outer layer.

14. A bandage as described in claim 10, with the said fasteners provided by lever clasps.

15. A bandage as described in claim 14, wherein a said fasteners is comprised of a U-shaped base element, of which the base plate is secured on the bandage structure through a pair of rivets, and the two side legs are provided with respective perforations in which a clamping lever is pivoted, said lever being constituted of a grip part for hand grasping, and a clamping part disposed at an angle thereto.

16. A bandage as described in claim 15, wherein the pivots are integral with the clamp element, and, on the grip part, to both sides there are respective integral cheek pieces bent at right angles thereto, which, upon gripping setting of the closure, externally embrace the legs of the U-shaped base member.

17. A bandage as defined in claim 1, wherein said grooves extend to margins of the inner layer.

18. A bandage as defined in claim 17, wherein said another end of each perforation is open onto said grooves to thereby collect the animal's sweat through said perforations into said grooves.

* * * * *